(12) United States Patent
Jedrzejewski

(10) Patent No.: US 9,950,136 B2
(45) Date of Patent: Apr. 24, 2018

(54) DEVICE FOR BODY RELAXATION AND RENEWAL

(71) Applicant: TISOFT WOJCIECH JEDRZEJEWSKI, Inowroclaw (PL)

(72) Inventor: Wojciech Jedrzejewski, Inowroclaw (PL)

(73) Assignee: TISOFT WOJCIECH JEDRZEJEWSKI, Inowroclaw (PL)

( * ) Notice: Subject to any disclaimer, the term of this patent is extended or adjusted under 35 U.S.C. 154(b) by 331 days.

(21) Appl. No.: 14/834,099

(22) Filed: Aug. 24, 2015

(65) Prior Publication Data

US 2017/0049990 A1  Feb. 23, 2017

(30) Foreign Application Priority Data

Aug. 22, 2015 (EP) .................................. 15460046

(51) Int. Cl.
*A61M 21/00* (2006.01)
*F21V 7/06* (2006.01)
*F21V 3/04* (2018.01)
*F21Y 105/00* (2016.01)

(52) U.S. Cl.
CPC ........... *A61M 21/00* (2013.01); *F21V 3/0418* (2013.01); *F21V 7/06* (2013.01); *A61M 2021/0005* (2013.01); *F21Y 2105/00* (2013.01)

(58) Field of Classification Search
CPC . A61M 21/00; A61M 2021/0005; F21V 7/06; F21V 3/0418; F21Y 2105/00
USPC .............................. 600/26, 27; 128/897–899
See application file for complete search history.

(56) References Cited

U.S. PATENT DOCUMENTS

| 4,130,120 | A |   | 12/1978 | Kohler, Jr. |            |
|-----------|---|---|---------|-------------|------------|
| 5,172,937 | A | * | 12/1992 | Sachetti    | A47G 9/0207 |
|           |   |   |         |             | 250/462.1  |
| 5,892,619 | A | * | 4/1999  | Chubb       | A41D 1/00  |
|           |   |   |         |             | 359/350    |
| 2006/0030907 | A1 | * | 2/2006 | McNew      | A61B 5/02405 |
|           |   |   |         |             | 607/88     |

(Continued)

FOREIGN PATENT DOCUMENTS

DE  24 38 164 A1  2/1976
DE  29 29 161 A1  2/1981

(Continued)

OTHER PUBLICATIONS

Machine English Translation of JPH0999106 (see attached as NPL).*

(Continued)

*Primary Examiner* — Navin Natnithithadha
*Assistant Examiner* — Sunita Reddy
(74) *Attorney, Agent, or Firm* — Katten Muchin Rosenman LLP

(57) ABSTRACT

A device for the body relaxation and renewal is described. It includes a perpendicular housing, which is a body with two side walls, a rear wall, and a front wall. The walls include vents situated in a lower and an upper part of said walls. A light panel is located inside at least one of said walls with alternately mounted fluorescent lamps and halogen lights. The fluorescent lamps are mounted in three rows of three pieces, in a vertical plane, one above another. The halogen lamps are set in slots mounted to vertical brackets and placed symmetrically in two vertical rows in three sections of two pieces.

5 Claims, 2 Drawing Sheets

(56) References Cited

U.S. PATENT DOCUMENTS

| | | | | |
|---|---|---|---|---|
| 2006/0064144 A1* | 3/2006 | Chen | .................... | A61N 5/0618 607/90 |
| 2008/0125620 A1* | 5/2008 | McNew | ................ | A61M 21/02 600/27 |
| 2010/0121420 A1* | 5/2010 | Fiset | ........................ | A61N 5/06 607/94 |
| 2010/0179469 A1* | 7/2010 | Hammond | ........... | A61N 5/0603 604/20 |
| 2010/0260669 A1* | 10/2010 | Yun | ..................... | A61K 31/137 424/1.49 |
| 2011/0040356 A1* | 2/2011 | Schiffer | ............... | A61N 5/0618 607/88 |
| 2012/0022618 A1* | 1/2012 | Lum | ................... | A61N 5/0616 607/90 |

FOREIGN PATENT DOCUMENTS

| | | |
|---|---|---|
| DE | 81 33 644 U1 | 3/1982 |
| DE | 43 37 982 A1 | 5/1995 |
| JP | H09 99106 A | 4/1997 |
| WO | 97/35640 A1 | 10/1997 |
| WO | 2006/015583 A2 | 2/2006 |

OTHER PUBLICATIONS

Machine English Translation of DE2929161 (see attached as NPL).*
European Search Report dated Feb. 2, 2016, from the corresponding EP Application No. EP 15 46 0046.4.

* cited by examiner

DEVICE FOR BODY RELAXATION AND RENEWAL

CROSS-REFERENCE TO RELATED APPLICATIONS

The instant application claims priority to European Patent Office Patent Application EP 15460046.4, filed on Aug. 22, 2015, presently pending, the contents of which are hereby incorporated by reference.

FIELD OF THE INVENTION

The subject of the invention is a home device destined for body relaxation and renewal. It occurs in a form of a panel equipped with integrated light sources of relaxation and therapeutic effect, which enables light radiation emission with parameters similar to sunlight parameters. This device is intended for being optionally placed especially in showers, bathrooms, relaxation and renewal areas, etc.

BACKGROUND OF THE INVENTION

Today's people's lifestyle is far from natural conditions. Access to natural sunlight in places of people's presence is significantly limited. Offices, production halls, storehouses, living space are lit mostly by the artificial light. This light approaches the color of sunlight only in the visible range. The remaining light spectrum is increasingly restricted in order to improve the efficiency of light sources.

Sunlight beneficially impacts human mood and health, among others. It is required for the synthesis of vitamin D3.

There are no similar solutions in current technology and economy.

SUMMARY OF THE INVENTION

The essence of the invention is the design of the device in the form of a light panel which can be mounted anywhere, for example as optional equipment in a shower cubicle. Inside this light panel there is a light module in the form of lamps mounted on the frame structure which are chosen and calibrated so as to emit light radiation with parameters similar to sunlight parameters. This light radiation, in 8-12 minutes, provides the body recommended daily dose of sunlight.

The sources of light in the light panels are halogen lamps with parabolic reflector and UV lamps in the form of mercury vapor fluorescent lamps emitting light having parameters similar to sunlight parameters. The total power of the light sources used in the light panel is chosen in such a way that it corresponds to the power spectrum of sunlight radiation in Central Europe—however, time of safe body exposure to sunlight depends on the climate zone and user's personal circumstances. Artificially, it is possible to receive the same dose in a shorter period of time by multiplying the intensity of the radiation sources. The intensity, spectral radiation composition, and its delivery time is controlled by the voltage regulator so that the light generated by the light panel has characteristics similar to sunlight. Moreover, the light (visible, ultraviolet and infrared) is also calibrated in order to obtain a composition of light as close as possible to natural sunlight and tailored to the user's health restrictions. Thanks to adjustment of radiation composition parameters are calibrated according to user's preferences.

| Band | Length [nm] | Irradiance [W/m2] | [%] |
|---|---|---|---|
| ultraviolet | <350 | 62 | 4.5 |
| near ultraviolet | 350-400 | 57 | 4.2 |
| visible | 400-700 | 522 | 38.2 |
| near-infrared | 700-1000 | 309 | 22.6 |
| infrared | >1000 | 417 | 30.5 |
| solar constant | | 1367 | 100 |

An advantage of the invention is the simplicity and versatility of the structure. The user at a specific time adopts the recommended daily radiation dose. Versatility is the ability to mount the light panels anywhere—without requiring separate room, for instant assembling the light panels in the shower cabin allows the simultaneous use of spa and a bath.

BRIEF DESCRIPTION OF DRAWINGS

The invention together with the above and other objects and advantages will be best understood from the following detailed description of the preferred embodiment of the invention shown in the accompanying drawings, wherein.

DETAILED DESCRIPTION

Figure 1:
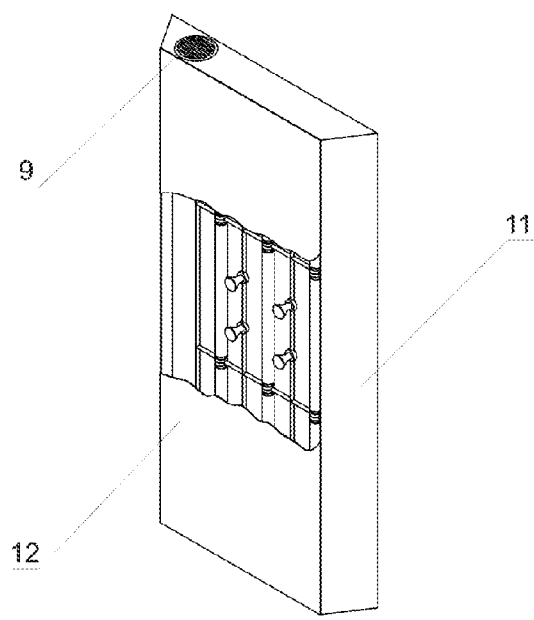
FIG. 1 depicts a view of one embodiment of a light panel used in the invention.
Figure 2:
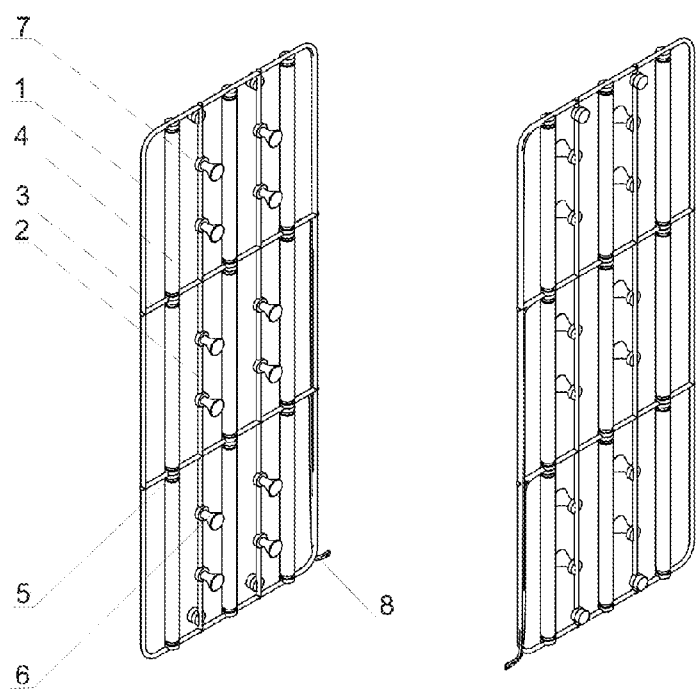
FIG. 2 depicts a cross-section view of an embodiment of a light module panel used in the invention.
Figure 3:
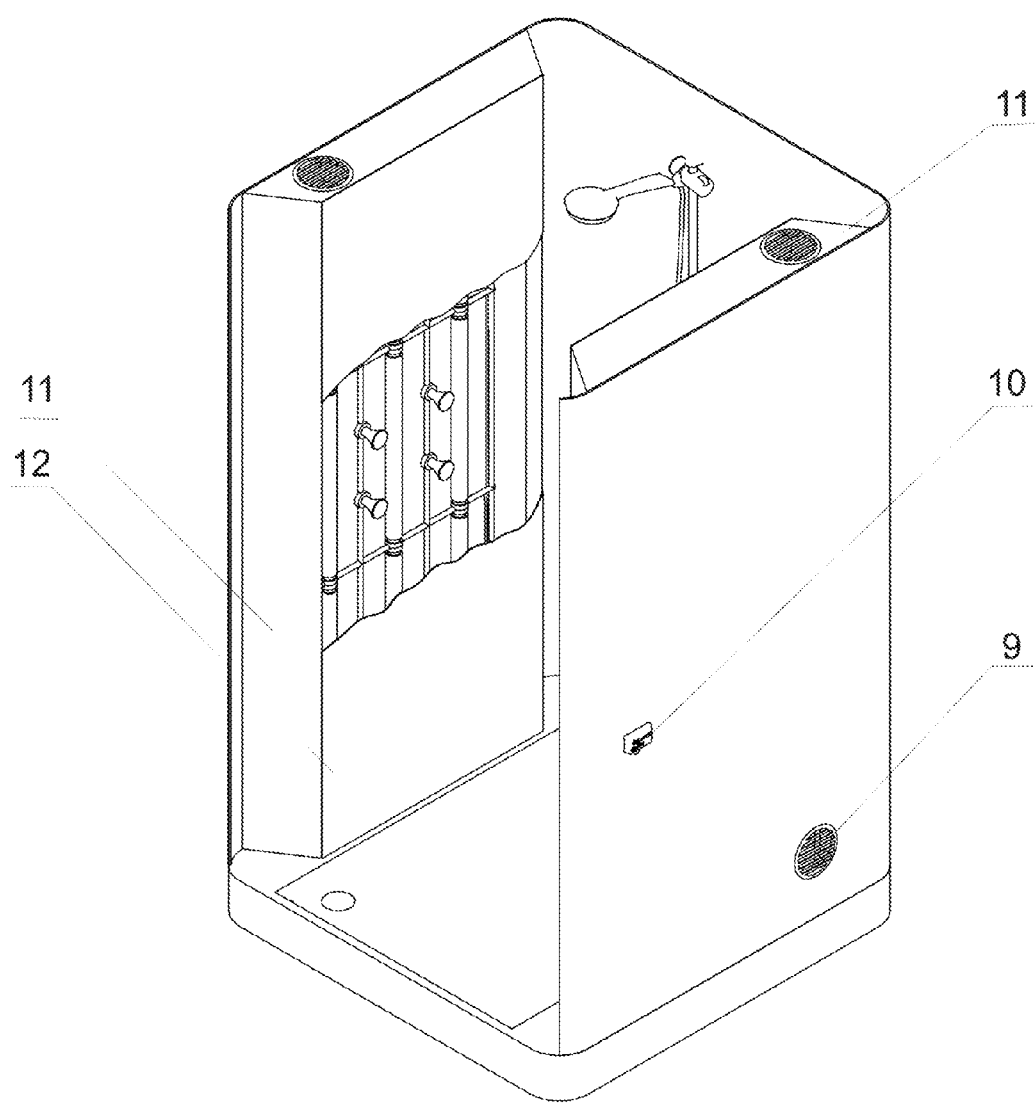
FIG. 3 depicts an overview of one embodiment of the invention.

The device is shown in more detail in the embodiment, of the example of integration light panels with a shower cabin which creates a home spa. In this example, FIG. 1 shows a light panel in partial section, FIG. 2 depicts the lightning module and FIG. 3 depicts light panels mounted in a shower cabin.

The light panel according to the invention is comprised of a rectangular housing, consisting of a body 11, a front wall 12, and a rectangular frame 1 located inside the housing, on which vertical stanchions 2 and horizontal stanchions 3 are mounted. On these stanchions, in a vertical plane, are mounted alternately four fluorescent lamps 4 and halogen lamps 6, as two lightning modules which emit light with intensity of 1.3 kW/m$^2$. The sources of light in the light panels are halogen lamps with parabolic reflectors and UV lamps in the form of mercury vapor fluorescent lamps emitting a light having parameters similar to sunlight parameters. The total power of the light sources used in the light panels is chosen in such a way that it corresponds to the power spectrum of sunlight radiation.

Fluorescent lamps 4 are mounted in three rows of 3 pieces, in a vertical plane, one above the other and they are placed in slots 5 which are applied to the horizontal stanchions 3. Halogen lamps 6 are mounted in the sockets 7 attached to the vertical stanchions 2, and the halogen lamps 6 are arranged symmetrically in two vertical rows of 3 sections of 2 pieces.

Halogen lamps 6 of the light panel produce the light with the aggregate intensity 1248 W/m$^2$ adequate sunlight irradiance value in IR band+band visible in Central Europe, and fluorescent lamps 4 emit ultraviolet radiation with intensity 119 W/m2 with UVB/UVA 2% ratio. Halogen bulbs scattering angle is 30°, and fluorescent lamps scattering angle is 120°.

The body 11 has rear and side walls which are made of plastic (e.g., polyvinyl chloride) and the front wall 12 is made of tempered quartz glass with the high transparency of visible light, UV light, and infrared light. The seal between front wall 12 and body 11 ensure the tightness of connected elements. The depth of the housing is 15 cm and ensures the safe distance between the lamps and the front wall 12 cover. And the vents 9 situated in lower—inlet and upper—outlet part of the body 11 remove the heat from the inside of the light panel and prevent excessive heating of the light panel.

The power leads 8 are situated in the rectangular frame 1 and taken outside the body 11 through the tight passages to the light controller 10.

The holes and mounting brackets of the body are mounted to the supporting structure of the shower.

In summary, the object—solved according to the invention—is a household device for relaxation and renewal of the body, which is a light panel equipped with integrated light sources having relaxation and healing effects, enabling light rays emitted with parameters similar to sunlight for optional equipment such as showers, bathrooms, relax and renewal areas, etc., composed of body 11 with the light module situated inside, characterized in that the light panel is composed of the body 11 and front wall 12 and has vents 9, situated in the lower and upper part, and has the light module in the shape of rectangular frame 1 inside with the vertical stanchions 2 and the horizontal stanchions 3 having the fluorescent lamps 4 and halogen lamps 6 mounted alternately in a vertical plane, wherein the fluorescent lamps 4 are mounted in three rows of 3 pieces, in vertical plane, one above another and set in slots 5, mounted to the horizontal stanchions 3, and halogen lamps 6 are set in sockets 7 mounted to the vertical stanchions 2 and placed symmetrically in 2 vertical rows in 3 sections of 2 pieces.

The invention claimed is:

1. A device for body relaxation and renewal comprising:
    a housing;
        wherein the housing comprises a body having two side walls, a rear wall, a front wall, and a top wall,
        wherein a first vent is located in the rear wall and a second vent is located in the top wall; and
    a light module,
        wherein the light module comprises a rectangular frame located between the front wall and the rear wall,
    wherein the frame has alternately mounted fluorescent lamps and halogen lamps;
    wherein the fluorescent lamps are mounted in three rows of three pieces, in a vertical plane, one above another and set in slots mounted on horizontal stanchions of the rectangular frame,
    wherein the halogen lamps are set in slots mounted to vertical stanchions of the rectangular frame, and
    wherein the halogen lamps are placed symmetrically in two vertical rows in three sections of two halogen lamps.

2. The device according to claim 1, wherein the rear wall and side walls of the body made from a plastic and the front wall comprises a cover made of quartz tempered glass with a high transparency to visible light, ultraviolet light, and infrared light.

3. The device according to claim 1, wherein a distance between the front wall and the rear wall is approximately 150 mm.

4. The device according to claim 1, wherein the fluorescent lamps emit light with parameters similar to sunlight, and
    wherein the halogen lamps have parabolic reflectors.

5. The device according to claim 1, wherein a scattering angle of the halogen lamps is 30° and a scattering angle of the fluorescent lamps is 120°.

* * * * *